United States Patent [19]
Piety et al.

[11] Patent Number: 5,922,963
[45] Date of Patent: Jul. 13, 1999

[54] DETERMINING NARROWBAND ENVELOPE ALARM LIMIT BASED ON MACHINE VIBRATION SPECTRA

[75] Inventors: Kenneth R. Piety; Mark W. Slemp; William F. Bethmann, Jr., all of Knoxville, Tenn.

[73] Assignee: CSI Technology, Inc., Wilmington, Del.

[21] Appl. No.: 08/874,333

[22] Filed: Jun. 13, 1997

[51] Int. Cl.[6] ........................... G01N 29/04; G01M 13/00
[52] U.S. Cl. ................ 73/659; 73/660; 73/602; 702/183
[58] Field of Search ............... 73/659, 660, 658, 73/579, 599, 602; 702/179, 180, 182, 183, 184, 185; 364/725.01, 726.01

[56] References Cited

U.S. PATENT DOCUMENTS

| | | | |
|---|---|---|---|
| 3,705,516 | 12/1972 | Reis | 73/659 |
| 4,322,976 | 4/1982 | Sisson et al. | 73/659 |
| 4,408,285 | 10/1983 | Sisson et al. | 364/508 |
| 4,425,798 | 1/1984 | Nagai et al. | 73/659 |
| 4,493,042 | 1/1985 | Shima et al. | 364/507 |
| 4,885,707 | 12/1989 | Nichol et al. | 364/551.01 |
| 4,980,844 | 12/1990 | Demjanenko et al. | 73/660 |
| 5,511,422 | 4/1996 | Hernandez | 73/593 |
| 5,602,757 | 2/1997 | Haseley et al. | 364/551.01 |
| 5,602,761 | 2/1997 | Spoerre et al. | 364/554 |
| 5,610,339 | 3/1997 | Haseley et al. | 73/660 |
| 5,646,350 | 7/1997 | Robinson et al. | 73/599 |
| 5,698,788 | 12/1997 | Mol et al. | 73/659 |

*Primary Examiner*—Hezron Williams
*Assistant Examiner*—Helen C. Kwok
*Attorney, Agent, or Firm*—Luedeka, Neely & Graham, P.C.

[57] ABSTRACT

The disclosed invention senses a machine's vibration spectrum, converts the vibration signal into a frequency-domain vibration spectrum, and analyzes the vibration spectrum to generate a narrowband alarm limit envelope against which the vibration spectrum of a previously uncharacterized machine may be compared. The limit envelope is generated from the test vibration spectrum of the machine which is the subject of the test, thus providing a performance benchmark against which to compare the vibration level of the previously uncharacterized machine. A limit envelope is also generated from a test vibration spectrum which has been designated as a reference or baseline spectrum. Further, a limit envelope is generated based upon a mean spectrum which is generated by combining several test vibration spectra. A limit envelope is also generated based upon mean and standard deviation spectra when a statistically significant number of test spectra are available.

19 Claims, 7 Drawing Sheets

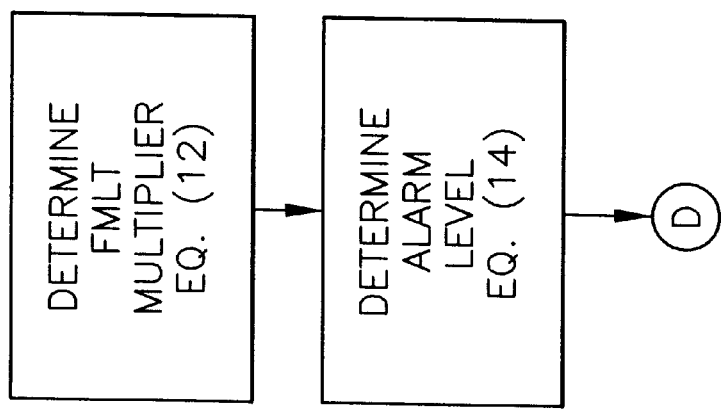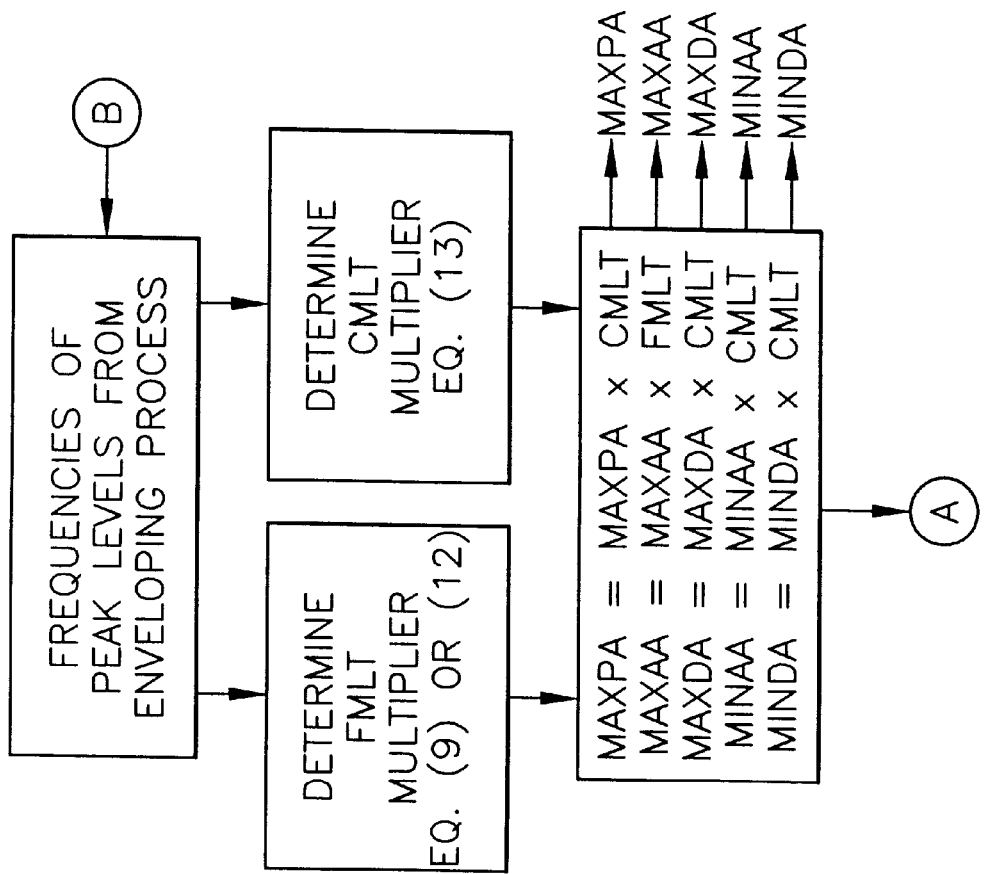
Fig. 6

DETERMINING NARROWBAND ENVELOPE ALARM LIMIT BASED ON MACHINE VIBRATION SPECTRA

BACKGROUND OF THE INVENTION

In a typical industrial setting, many types of rotating machinery are employed to provide the mechanical and other driving forces necessary for production. Over time, rotating and other structural elements of the machine degrade and fault conditions develop which may eventually lead to significant degradation of the machine's output or catastrophic failure of the machine. When a machine fault leads to stoppage of the machine, the resultant loss in productivity can be very costly to the company. Accordingly, proper maintenance of machinery is an important aspect of many industrial facilities.

Non-destructive, predictive maintenance of industrial machinery is often used to identify faulty machines so that machine "down-time" can be scheduled in a manner that minimizes any negative effect to manufacturing operations. Many predictive maintenance methods are employed to ascertain a machine's health. Arguably, the most effective analytical technique for identifying faults in rotating machinery involves the use of narrowband envelope alarm limits. By using an envelope alarm limit as a basis for which to compare a vibration spectrum, exceptions can be identified which are directly associated with specific fault conditions. Examples of such exceptions include individual spectral peaks which exceed the alarm limit envelope, and families of related peaks whose total energy exceeds the alarm limit envelope. The magnitude and frequency of these exceptions can be used by an analyst or an automated diagnostic system to identify the type and severity of a fault. In the past, exceptions analysis techniques have relied on alarm limits that are defined for certain frequency regions of the spectrum. One example is the case where a single alarm value is applied to the overall level of vibration of an entire spectrum. In this example, the energy of a given vibration spectrum is summed over the entire frequency region and compared to a single, overall alarm limit. Historically, vibration analysis software packages have also allowed the specification of separate frequency bands for which parameter values can be calculated. These parameter values can then be compared to their individual, separately defined alarm limit.

Many benefits are realized from the use of narrowband envelope alarming (NEA). The NEA approach allows the analyst to maintain maximum sensitivity to all types of fault conditions (e.g., high power, low power, etc.) anywhere in the frequency range. In contrast, broadband analysis techniques can easily mask certain types of faults. Narrowband envelope alarming provides better diagnosis and identification of faults since it identifies precise frequencies at which an anomalous condition is occurring, which is the basis of an accurate diagnosis of the fault condition. Additionally, NEA produces data which can be analyzed to obtain a more accurate assessment/valuation of fault severity.

While many benefits can be realized from the use of an NEA technique, there are also substantial difficulties and disadvantages associated with currently known NEA techniques. For example, establishing individual alarm values manually for every envelope window is a very tedious (if not impossible), labor-intensive process, and there is no accepted methodology for creating the envelope limits. Even computer-assisted methods of determining a narrowband envelope can require tremendous amounts of data over a complete range of operational states to be monitored, and the required data will typically have to be acquired during manual periodic survey programs over extended periods of time. Moreover, there is currently no well-established method for turning the population of data into effective narrowband envelopes.

An inappropriate NEA will generate many false alarms. False alarms can result since there are many variables being tested and the process is highly dependent on accurate RPM values for each spectrum, which are commonly not measured when the spectrum is collected. Additionally, purely statistical methods for performing NEA can be easily corrupted by the inclusion of bad data (i.e., spectra representing fault conditions) in the analyzed population.

The many pitfalls and enormous labor involved with constructing appropriate narrowband envelopes has prevented, or at least significantly limited, application of NEA techniques by vibration analysis practitioners. Accordingly, what is needed is a method and apparatus for easily and effectively developing accurate narrowband envelopes for identification of faults in rotating machinery, regardless of the amount of historical spectral vibration data that is available to construct the narrowband envelope.

SUMMARY OF THE INVENTION

With regard to the foregoing and other objects, the invention in one aspect provides a method for constructing an alarm limit envelope for spectral analysis of vibration data collected from a machine where the alarm limit envelope is constructed from a single machine vibration spectrum. This method, which is particularly applicable to machines for which little or no historical vibration data is available, includes the steps of measuring vibration generated by the machine over time to produce a time series of vibration data measurements. The time series of vibration data measurements are transformed from the time domain to the frequency domain to produce a single vibration spectrum containing a plurality of peaks, where each peak has an amplitude and a frequency associated with it. The vibration spectrum is divided into a plurality of frequency windows, and an alarm limit value is calculated for each window. Each alarm limit value represents a maximum vibration level above which the machine's vibration level is considered abnormal for the range of frequencies included within the particular window.

Each alarm limit value is determined by calculating several candidate limits based upon several heuristically-developed construction parameters, and then choosing the appropriate limit level from the candidate limits. The value of each of the construction parameters is user-adjustable based upon engineering judgement. At least one multiplier is determined for each candidate alarm limit and used to adjust the candidate alarm limit to produce a plurality of adjusted candidate alarm limits for each window. The multiplier(s), which are based on characteristics specific to the vibration peak within the window, are determined in such a manner that a conservative adjustment of the candidate alarm limit is made. In other words, the adjustment of the candidate alarm limits in accordance with the multipliers is such that the alarm limits are either unchanged or are made to provide a more inclusive indication of potential machine faults. For each window, one of the adjusted candidate alarm limits is then selected to be the alarm limit value for the window. The selection of the appropriate alarm limit level depends upon the amplitude of the spectral peak from the construction spectrum and upon the values of the construction parameters which the user has selected. All of the alarm values collectively represent the alarm limit envelope.

In accordance with another aspect of the invention, a method is provided for constructing an alarm limit based on a plurality of machine vibration spectra. This method is applicable to machines for which some historical vibration data is available (or can be extrapolated from other similar machines) but an insufficient amount of historical data is available to be considered statistically significant. The steps of this method include providing a plurality of vibration spectra corresponding to vibration generated by at least one machine. Each of the vibration spectra provided will include a plurality of peaks where each peak has an amplitude component and a frequency component. A mean vibration spectrum is determined where each amplitude of the mean spectrum represents the statistical mean of all corresponding amplitudes of the plurality of vibration spectra. The mean vibration spectrum is divided into a plurality of frequency windows, and an alarm limit value is calculated for each window. Each alarm limit value represents a maximum vibration level above which the machine's vibration level is considered abnormal for the range of frequencies included in the particular window.

To calculate an alarm limit value, a plurality of candidate alarm limits are determined for each window. One of the candidate alarm limits is then selected to be the alarm limit value for the window. The alarm limit values for all windows collectively comprise the alarm limit envelope.

The invention also provides a method for constructing an alarm limit envelope for machines having a statistically significant amount of historical vibration data available. In this method, two statistically derived spectra are calculated from the historical vibration spectra—a mean vibration spectrum and a standard deviation spectrum. The mean vibration spectrum is divided into a plurality of frequency windows, and an alarm limit value is calculated for each window. The alarm limit value for each window is calculated by determining several candidate alarm limits based upon heuristically-developed construction parameters as discussed above, and by determining at least one candidate alarm limit based upon the mean and standard deviation values within a particular window. The candidate alarm limit based upon the mean and standard deviation data provides an accurate limit when a statistically significant sample of acceptable machine vibration spectra is available. By choosing between the statistically-based alarm limit and alarm limits based upon heuristically-developed construction parameters, the invention superimposes engineering logic on the true machine behavior represented by the collection of vibration spectra.

The present invention also provides a procedure for limiting or negating the impact of data values which fall outside a user-selected number of standard deviations when constructing an envelope based on a collection of spectra. Using this procedure, the user may specify the conservativeness of the mean and standard deviation values used in the envelope construction.

BRIEF DESCRIPTION OF THE DRAWINGS

The invention will now be described in further detail with reference to the drawings, wherein like reference characters designate like or similar elements throughout the several drawings as follows:

FIG. 6 is a flow diagram of a profiler process according to the present invention.

DETAILED DESCRIPTION OF THE PREFERRED EMBODIMENT

Figure 1:
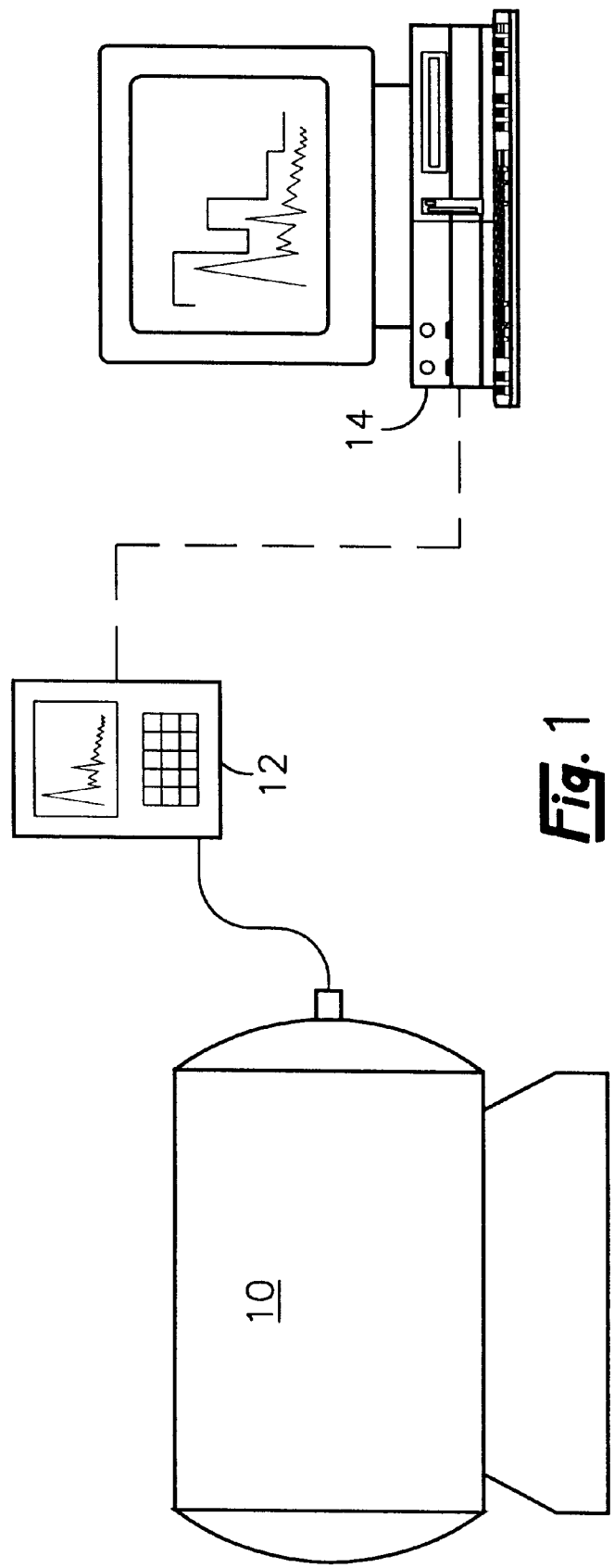
FIG. 1 is a diagram of a machine vibration monitoring system in accordance with the present invention.

A machine vibration monitoring system, as shown in FIG. 1, is used by machine maintenance personnel to measure and analyze the vibration level of a machine 10 as part of a machine monitoring program. By monitoring vibration spectra, the operational condition of one or more such machines may be deduced. Typically, such a system includes a device, such as the portable vibration analyzer 12 shown in FIG. 1, which collects, stores, and analyzes vibration data from several different machines, and a base computer 14 which further analyzes the vibration data after the data has been downloaded from the portable vibration analyzer 12. The analysis performed by the base computer 14 and the portable vibration analyzer 12 includes processes, carried out by software instructions, which convert the vibration data into vibration frequency spectra, determine if the machine's vibration level has exceeded defined limits, and report to the machine maintenance personnel whether the limits have been exceeded by the measured data. The processes of the current invention determine narrowband alarm limit envelopes which are constructed from the machine's measured vibration spectra. These envelope functions define vibration amplitude limits above which the machine's vibration levels are considered abnormal.

The narrowband envelope alarm limit construction processes of the present invention allow the creation of reasonable envelope limits regardless of the amount of vibration data which has been previously measured during the course of the machine monitoring program. The invention uses three different techniques for constructing an alarm limit envelope, such that machine performance can be effectively monitored in all phases of a machine monitoring program. One technique is used during the period prior to the availability of a reference spectrum. A second technique is used when a reference spectrum is available which represents an acceptable operating condition of a machine. A third technique is used when a significant amount and quality of historical vibration data is available. These three techniques for envelope construction are disclosed in detail hereinafter.

During the initial startup of a machine monitoring program, essentially no information is available concerning the operating condition of the machinery. When a machine is monitored for the first time, no previous data is available to serve as a baseline or reference to which a measured vibration spectrum can be compared. At this point, the level of vibration that represents normal, fault-free machine operation is unknown. In this situation, the process of the present invention utilizes essentially any measured vibration spectrum which the user designates as a basis for envelope construction, even though it is unknown whether the machine from which the data was measured has a fault present. When an envelope is constructed for such an initial vibration spectrum, the "profiler" process is invoked. This process, which is described in detail hereinafter, utilizes the measured spectrum to create a conservative narrowband envelope limit using heuristically developed shaping parameters in conjunction with user-defined construction parameters. The operator may also invoke the profiler process to determine and use the profiler parameters to generate a conservative envelope regardless of whether or not the vibration spectrum being used to construct the envelope has been previously designated as the reference spectrum. In later stages of the machine monitoring program, if a previously constructed envelope spectrum does not extend to the upper and lower frequencies of the test spectrum, then the profiler process will be called to construct an envelope limit for the peaks that are present in the uncovered portion of the spectrum.

When the user has developed confidence that a measured machine vibration spectrum accurately represents the nominal levels of vibration that are associated with normal machine operation, the user designates the measured spectrum as a reference or baseline spectrum. At this point, the second envelope construction technique of the present invention is used to generate a limit envelope based upon user-defined construction parameters. In this situation, the conservative shaping parameters of the profiler process are not necessary, and are not used in envelope construction unless the user desires to do so.

The third technique provided by the present invention incorporates additional criteria established from measures of the statistical mean and standard deviation of the vibration spectra to construct an envelope limit. This involves a statistical construction technique requiring that enough spectral data has been collected on a given machine so that a relatively accurate representation of the behavior of the machine can be formulated. Since this technique relies on the use of statistical analysis, it will generate the most effective envelope alarm limit when a high number of spectral data samples are included in the analysis. If a machine monitoring program is relatively immature, such that a low number of routine measurement surveys have been performed, then machines can be grouped together into analysis groups so that the statistical analysis becomes more effective in a shorter time. The grouping allows the data from "similar" machines to be combined in the construction of an envelope limit. This envelope limit can then be applied to all of the measurement locations from which data was collected for the envelope construction.

Once envelopes have been generated which accurately indicate a limit for acceptable machine performance, these envelopes are stored in the computer memory 42, the measurement device memory 24, or on a storage device 16, 34. These limit envelopes are then used as standards against which to compare machine performance as the conditions of the machines change over time. As mentioned previously, a particular envelope which has been constructed based on spectra measured on a family of similar machines may be used as a standard for all the machines in the family. Additionally, that envelope may be used as a standard for any new or previously-uncharaterized machine which would be included in the same family due to its physical characteristics. In this manner, the present invention can be used to build a data base of limit envelopes which can be used as standards to assess the performance of a variety of machine types.

Envelope Construction Based on an Initial Measured Spectrum

Figure 2:
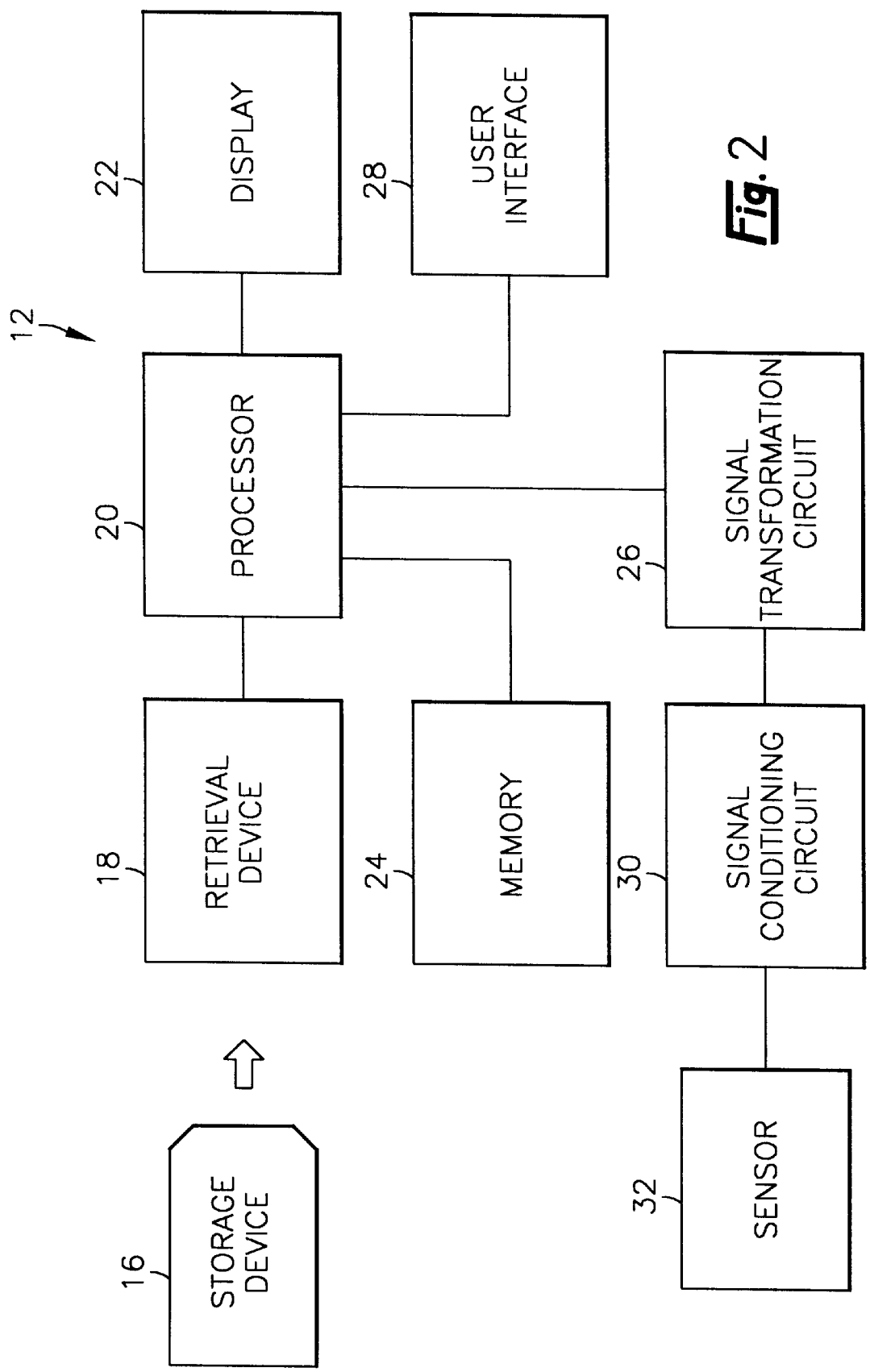
FIG. 2 is a functional diagram showing the components of a device for measuring and analyzing machine vibration spectra.

With reference now to FIGS. 1 and 2, the preferred embodiment of the invention will be described. When a machine's vibration level is evaluated for the first time, an operator places a sensor 32 of the portable vibration analyzer 12 against the machine housing in a location on the machine 10 where a characteristic vibration can be measured. The sensor 32, such as an accelerometer, converts the machine's mechanical vibration into an electrical signal representing the machine's vibration level. A signal conditioning circuit 30 filters, amplifies, and converts the electrical vibration signal into a format which can be digitally processed. A signal transformation circuit 26 transforms the time-domain electrical vibration signal into a frequency-domain vibration spectrum representing the vibration signal measured by the sensor 32. The portable vibration analyzer 12 includes memory 24 in which the vibration spectrum data is stored until such time that the processor 20 is commanded to transfer the vibration spectrum data from the memory 24 to another device, such as the base computer 14.

Figure 3:
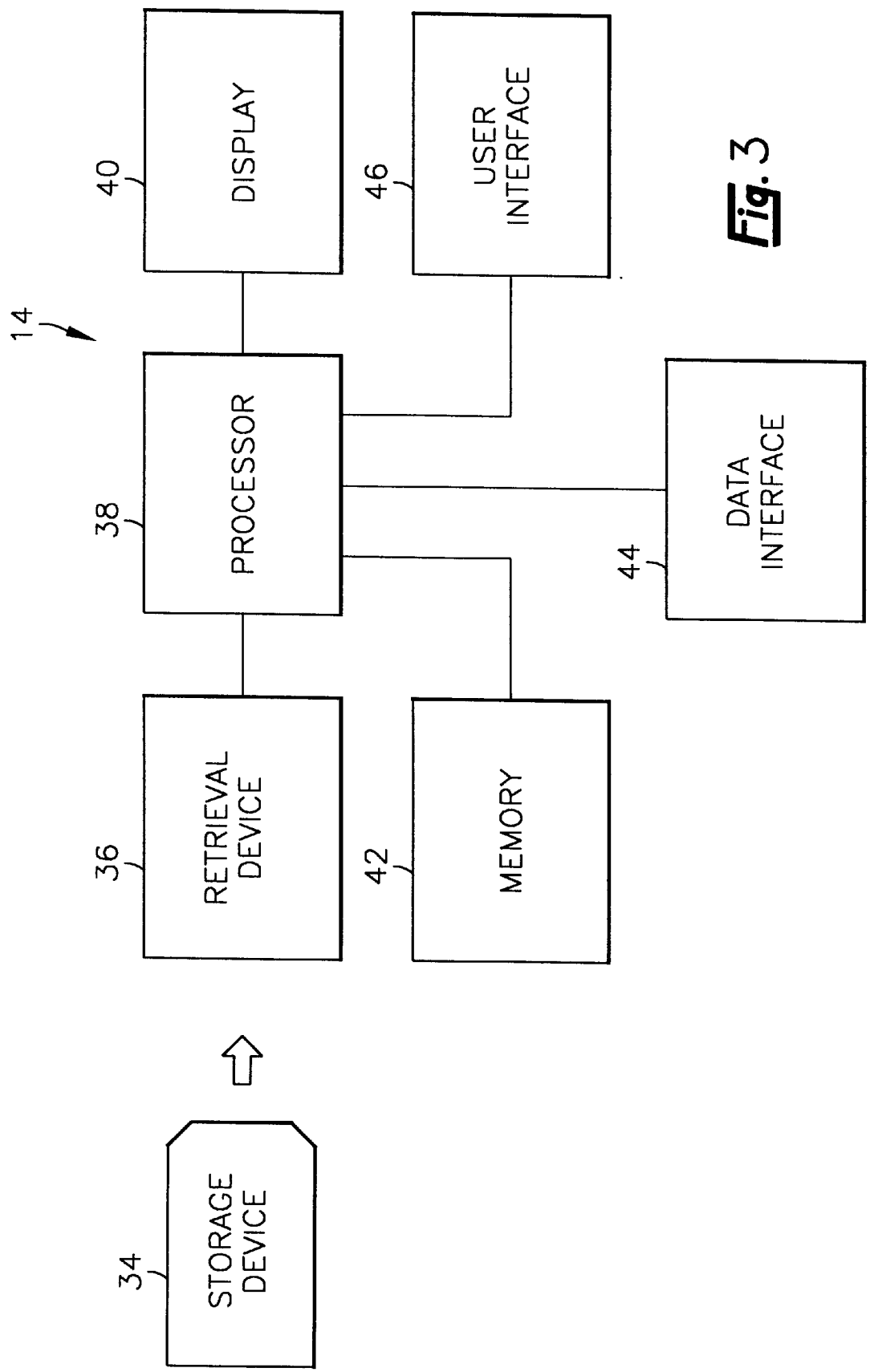
FIG. 3 is a functional diagram showing the components of a device for determining narrowband alarm limit envelopes based upon machine vibration spectra.

As shown in FIG. 3, the base computer 14, such as a desktop or laptop PC, includes a processor 38, memory 42, a user interface 46, such as a keyboard and mouse, and a display 40. The base computer processor 38 performs the narrowband alarm limit envelope construction processes which are described hereinafter. The base computer memory 42 stores the computer programs used to control these processes, the measured vibration spectra, and the envelope function data. Alternatively, the computer programs used to control the processes are stored on a storage device 34, such as a magnetic disk or tape, and are retrieved by a retrieval device 36, such as a disk drive or tape drive, for use in the processor 38. The user interface 46 provides for operator control over the data manipulation processes, and the display 40 provides the visual representations necessary to control the processes and to view the results of the processes.

Once the measured vibration spectrum data has been measured and stored in the base computer memory 42, the processor 38 constructs a limit envelope from the measured spectrum. Since the measured data in this situation is the initial spectrum, and no reference spectrum exists for this machine, the profiler process is invoked to generate an alarm limit envelope. The measured spectrum used to construct the envelope consists of a number of data points, each point representing a vibration level at a particular vibration frequency. For purposes of the envelope construction process, vibration amplitude is expressed in units of velocity, such as inches per second, although the vibration amplitude may also be expressed in units of displacement or acceleration when displayed to the user. Vibration frequency is expressed in Hertz.

Figure 5:
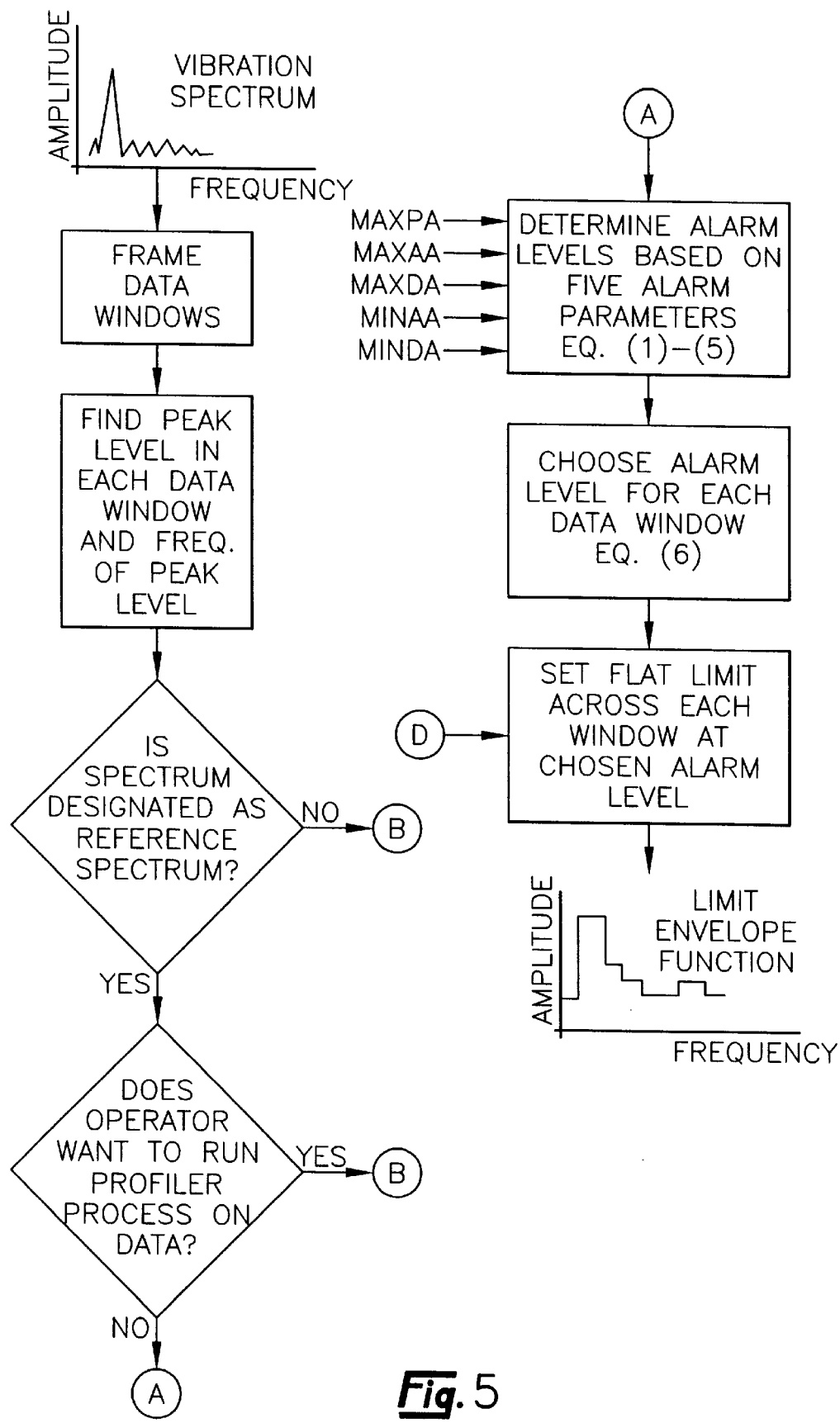
FIG. 5 is a flow diagram of an alarm limit enveloping process according to the present invention.

As shown in FIG. 5, the envelope construction process begins by framing a number of data windows across the frequency spectrum and looking for the peak vibration level within each window. In the preferred embodiment of the invention, the width of a data window is either a fixed number of data points or a number of data points that is based on a fixed percentage of the frequency at which a given envelope window begins. The user may specify which type of window (fixed delta or fixed percentage) and the number of data points or the percentage value that is to be used. If the fixed-percentage approach is selected, window width can be determined by dividing the window frequency by the highest frequency in the spectrum, and then multiplying this ratio by the total number of lines of resolution. Each data point within a window corresponds to the spectral value for a given line of resolution on the frequency axis.

Once the nominal window width is set, the process steps from point to point within each data window, comparing the vibration level of each point to the adjacent points. The largest data point value within the data window is considered to be the peak vibration level. If the largest data point value is found within two data points of the right side of the data window, then the width of the data window is increased by one half of its initial width. This ensures that a data window encloses an entire peak so that a single limit is applied to the window. This technique also allows the frequency of an individual peak to shift up to two resolution lines in either direction and still have the appropriate limit applied. This shift could commonly be a result of the incorrect specification or calculation of the machine's running speed in the order-normalizing process discussed below.

The initial envelope construction process next determines an alarm level corresponding to each peak vibration level for each data window across the entire frequency range of the spectrum being used to construct the envelope. For the peak level of vibration within a given data window, the process chooses one of five possible alarm levels which have been calculated using five different alarm parameters. These alarm parameters include the maximum percent alarm (MAXPA), the maximum absolute alarm (MAXAA), the maximum delta alarm (MAXDA), the minimum absolute alarm (MINAA), and the minimum delta alarm (MINDA).

MAXPA is expressed as a percentage of the peak vibration level detected within a given data window. This percentage multiplier is generally set at between 400 to 800%. Using A, the alarm level is determined using the following equation:

$$AL_{MAXPA} = \frac{MAXPA \times CMLT}{100} \times PVL \quad (1)$$

where $AL_{MAXPA}$ is the alarm level determined using MAXPA, PVL is the peak vibration level within a data window, and CMLT is a multiplier which decreases the alarm level to provide a more conservative limit when the condition of the machine is unknown. (The determination of CMLT is described in detail below.) For example, with a detected peak vibration level of 0.10 inches per second (ips), MAXPA of 500%, and CMLT of 1.0 the alarm limit would be 0.50 ips.

MAXAA defines an absolute alarm level that is constant across the spectrum though it is applied to each individual data window. The value of MAXAA is independent of the peak vibration level within each data window. If expressed in velocity units, this limit is generally set to between 0.2 and 0.5 ips. This limit may also be expressed as a percentage of a predetermined overall alert level, such as may be defined in a pre-existing data base, in which case the percentage is generally specified between 80 to 120% of the overall alert level. With MAXAA expressed as a percentage, the alarm level is determined by:

$$AL_{MAXPA} = \frac{MAXAA \times FMLT}{100} \times OAL \quad (2)$$

where $AL_{MAXAA}$ is the alarm level determined using MAXAA, OAL is the overall alert level, and FMLT is a another multiplier which decreases the alarm level to provide a more conservative limit when the condition of the machine is unknown. (The determination of FMLT is described in detail below.)

MAXDA defines a value which is added to the peak vibration level within the data window to set the alarm limit. This value is also either specified as a percentage of the overall alert level or in velocity units. If expressed as a percentage, it is generally between 15 to 30% of the overall alert level, and if expressed in velocity, it is typically between 0.05 and 0.15 ips. Using MAXDA expressed as a percentage, the alarm level is:

$$AL_{MAXDA} = \left(\frac{MAXDA \times CMLT}{100} \times OAL\right) + PVL \quad (3)$$

where $AL_{MAXDA}$ is the alarm level determined using MAXDA.

MINAA is a minimum absolute alarm which defines a minimum alarm level permitted for an envelope spectrum. Expressed as a percentage, it is commonly between 0.1 and 0.5% of the overall alert level. If expressed in velocity units, it is typically specified as between 0.0001 and 0.005 ips. Where MINAA is expressed as a percentage, the alarm level is:

$$AL_{MINAA} = \frac{MINAA \times CMLT}{100} \times OAL \quad (4)$$

where $AL_{MINAA}$ is the alarm level determined using MINAA.

MINDA defines a value which is subtracted from the peak vibration level within the data window to set a minimum alarm limit. If expressed as a percentage, it is generally set to between 0.1 and 0.5% of the overall alert level, and if expressed in velocity, it is typically between 0.0005 and 0.001 ips. Using MINDA expressed as a percentage, the alarm level is:

$$AL_{MINDA} = \left(\frac{MINDA \times CMLT}{100} \times OAL\right) \quad (5)$$

where $AL_{MINDA}$ is the alarm level determined using MINDA.

The alarm limit enveloping process defines an alarm level individually for each data window by choosing a level determined using one of these five alarm parameters. For each identified vibration level peak, the process determines the values using each of the five parameters and chooses either the lowest value of the alarm level determined using MAXPA, MAXAA, and MAXDA, or the highest value of the alarm level determined using MINAA and MINDA, whichever is greater, as the alarm limit for that data window. Expressed in equation form, the alarm limit, AL, is:

$$AL = \max(\min(AL_{MAXPA}, AL_{MAXAA}, AL_{MAXDA}) \max(AL_{MINAA}, AL_{MINDA})) \quad (6)$$

As previously discussed, the profiler process modifies the alarm limit envelope values by multiplying the envelope construction parameters by heuristically developed shaping parameters, FMLT or CMLT, when the alarm limit envelope is being constructed using a newly-measured vibration spectrum, so that exceptions in the construction spectrum are detected. Since the condition of the machine from which the construction spectrum was taken is not known, the profiler multipliers conservatively shape the maximum allowable alarm level for each window. As described below, the value of FMLT is a function of whether the data window contains synchronous or nonsynchronous frequencies. This is a result of the fact that in a velocity vibration spectrum, peaks of higher amplitudes generally occur in the lower frequency harmonics of a machine's running speed. Both profiler multipliers also take into account the absolute frequency of the window for which a limit is being constructed. This absolute frequency shaping is designed to take into account the fact that the velocity response function rolls off at very low frequencies and also very high frequencies. The profiler multiplier shaping is also a function of the nominal level of vibration that the user expects from a given machine. This estimate of the overall vibration level depends on whether the user considers it to be a rough, average, or smooth running machine.

To determine whether the frequency corresponding to the first data point of a data window is synchronous, the profiler process first determines the order of the data point as follows:

$$\text{ORDER} = \frac{FREQ}{MRPS} \tag{7}$$

where FREQ is the frequency in Hertz of the highest-amplitude data point in the data window, and MRPS is the machine running speed in Hertz. The data point is at a synchronous frequency if the value of ORDER is within a certain tolerance of an integer number, where the tolerance is frequency dependent. This is necessary since discrepancies in the specification or calculation of MRPS are magnified at higher frequencies. For a given ORDER, if the following equation is true, then the data point is synchronous:

$$|\text{ORDER-NIV}| \leq \text{TOL} \tag{8}$$

where NIV is the nearest integer to ORDER, and TOL is the order tolerance which is order-dependent as follows:
TOL=0.025 for ORDER≦10
TOL=0.040 for 10<ORDER≦25
TOL 0.060 for ORDER>25
For example, if the order of the selected point were 1.01, then the data window would be considered synchronous since 1.01−1=0.01, and 0.01 is less than the order tolerance of 0.025. However, if the order of the data point were 17.05, then the data point would be asynchronous since 17.05−17= 0.05, and 0.05 is not less than the order tolerance of 0.040.

If the frequency of the highest-amplitude data point in a data window is synchronous, then the value of FMLT is expressed as:

$$\text{FMLT=FACSYN} \times \text{PRFILE} \times \text{FREQSHAPE} \tag{9}$$

where the value of FACSYN depends upon the order as indicated in Table 1.

TABLE 1

| ORDER | FACSYN |
|---|---|
| 1 | 0.60 |
| 2 | 0.40 |
| 3 | 0.30 |
| 4–10 | 0.25 |
| 11–20 | 0.20 |
| >20 | 0.15 |

The value assigned to PRFILE is operator-selectable. As discussed previously, this value sets the overall sensitivity of the alarm construction process by allowing the operator to designate the expected vibration level of the machine using one of the levels indicated in Table 2.

TABLE 2

| Nominal Vibration Level | PRFILE |
|---|---|
| Smooth | 0.667 |
| Average | 1.0 |
| Rough | 1.5 |

FREQSHAPE is a scale factor that rolls off the value of FMLT at the low and high ends of the vibration spectrum. If the highest frequency of a data window is less than FLOW (2 HZ typical) then FREQSHAPE is determined by:

$$FREQ\text{SHAPE} = \frac{FREQ}{FLOW} \tag{10}$$

where FREQ and FLOW are expressed in units of Hertz. If all of the frequencies within a data window are greater than FLOW but less than FHI (2500 HZ typical), then the value of FREQSHAPE is one. If the lowest frequency of a data window is greater than FHI, then FREQSHAPE is determined by:

$$FREQ\text{SHAPE} = \frac{FHI}{FREQ} \tag{11}$$

where FREQ and FHI have units of Hertz.

If the peak is asynchronous, then FMLT is expressed as:

$$\text{FMLT=FACNSY} \times \text{PRFILE} \times \text{FREQSHAPE} \tag{12}$$

The value of FACNSY in equation (12) is a function of the order of the data window as indicated in Table 3.

TABLE 3

| ORDER | FACNSY |
|---|---|
| 1 | 0.30 |
| 2–3 | 0.25 |
| 4–10 | 0.20 |
| 11 and greater | 0.10 |

For synchronous and asynchronous peaks, the value of the multiplier CMLT is expressed as:

$$\text{CMLT=FREQSHAPE} \tag{13}$$

where FREQSHAPE is determined by equation (11).

In situations where an operator measures vibration data on a machine for which an alarm limit envelope already exists, and the operator chooses to collect the new vibration data over a frequency range which extends below the minimum frequency and/or above the maximum frequency of the envelope created from the reference spectrum, then the profiler process is invoked. In order to analyze the entire frequency range of the test spectrum, a limit level to which the test spectra can be compared must exist across the entire frequency range. The profiler process determines an envelope alarm limit for peaks which are located in regions which are not covered by the original envelope limit. The profiler process determines the envelope alarm limit, AL, for a peak in these regions by the following equation:

$$AL = FMLT \times MAXAA \quad (14)$$

where FMLT is determined as in equation (12) for asynchronous peaks, and MAXAA is the maximum absolute alarm parameter as described previously.

Figure 4:
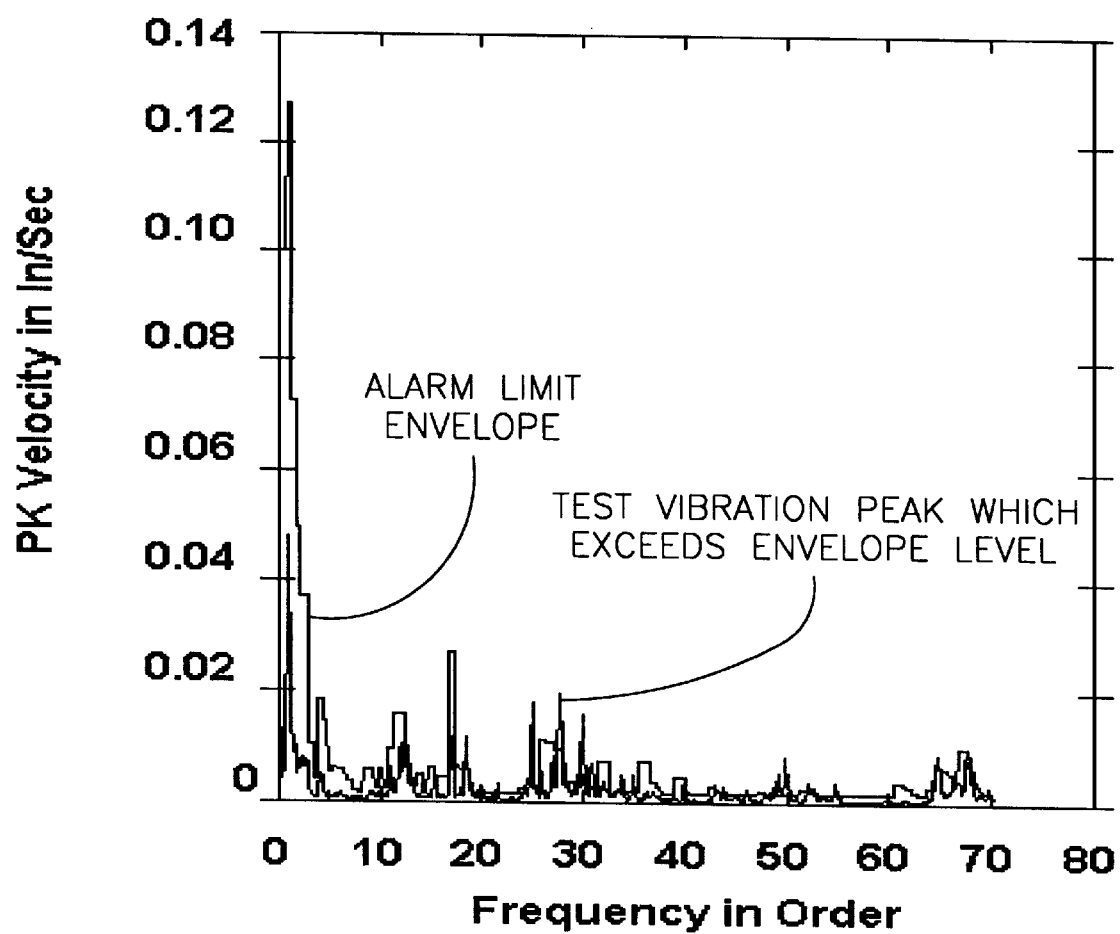
FIG. 4 is diagram showing an alarm limit envelope overlaying a test vibration spectrum.

Once the alarm limit value has been defined for each data window, the alarm limit envelope is constructed by setting the limit value at each data point within a data window to the alarm level which was defined for that window. In this way, the envelope is flat across each data window with a discontinuity (either a step up or a step down) at the transition from one window to an adjacent window. An example of such an alarm limit envelope is shown in FIG. 4. In the preferred embodiment of the invention, this envelope function is identified as being associated with a particular machine and is stored in memory 42 within the base computer 14.

Envelope Construction Based on Reference Spectrum

At a second stage in the machine monitoring program, when an operator is confident that a measured vibration spectrum represents nominal levels of vibration that are associated with the machine during normal operation, the operator may designate the measured vibration spectrum to be a reference or baseline spectrum. When the base computer processor 38 constructs an alarm limit envelope based on the designated reference spectrum, the envelope construction process constructs an envelope in the same manner as discussed above except that the profiler process multipliers, FMLT and CMLT, are set to unity. In this manner, the alarm limit envelope is constructed from the reference spectrum without the conservative shaping introduced by the profiler process, unless the operator specifically requests that the profiler process be invoked.

Statistical Envelope Construction

The statistical envelope construction process is invoked by the user when a number of spectra have been collected as part of the routine measurement surveys made during a machine monitoring program. The specific number of surveys that should be performed before this phase of the process is invoked depends on the decision of the user to group similar machines and/or points together so that more data is available for envelope construction. Since the exact time when enough spectrum samples have been collected is not precisely known to the user, the statistical envelope construction process is subdivided into two different construction techniques, the choice of which is transparent to the user.

The first technique for determining a statistical envelope limit protects against the situation where a number of data sets have been collected, but the computed mean and sigma do not seem to be representative of the true population, where the population represents the range of acceptable operational vibration levels of the machine or machines for which envelope limits are being constructed. In this situation, the standard deviation of the data is likely to be invalid. For this envelope construction technique, the mean spectrum simply replaces the reference spectrum in the process discussed previously. The same five envelope construction parameters that were used to calculate the limit for each data window when using a reference spectrum as the basis for construction are applied to the mean spectrum. In this process, the mean spectrum is represented by individual mean and sigma values calculated for each line of resolution in the spectra.

The second technique for determining a statistical envelope limit incorporates the use of the calculated standard deviation values as well as the mean values for each line of the mean spectrum. In the preferred embodiment of the invention, the number of spectra required before this technique is implemented is 16. In this process, an additional (sixth) envelope construction parameter is used to determine an alarm limit level based on the calculated mean and standard deviation values for each of the spectral lines within a given data window. The standard deviation alarm, SDA, is a user-selectable value which specifies the number of standard deviations that are added to the mean vibration peak value to set an alarm limit for the particular data window. Using SDA, an alarm level is calculated for each data point in the data window by the following equation:

$$AL_{SDA} = MEAN + (SDA \times STANDEV) \quad (15)$$

where $AL_{SDA}$ is the alarm limit determined using SDA, MEAN is the vibration level at the corresponding data point in the mean spectrum data window, and STANDEV is the vibration level at the corresponding data point in the standard deviation spectrum data window. The largest calculated value of $AL_{SDA}$ for all of the points within the data window is selected as the $AL_{SDA}$ for the window.

As with the envelope construction process described previously using a single initial vibration spectrum, this second technique for statistical envelope construction defines an alarm limit individually for each data window of the mean spectrum by choosing a level determined using one of the five alarm parameters described previously, or using SDA. For each identified vibration level peak, the process determines six alarm levels using each of the six parameters, and chooses either the lowest value of the alarm level determined using MAXPA, MAXAA, MAXDA, and SDA, or the highest value of the alarm level determined using MINAA and MINDA, whichever is greater, as the alarm limit for that data window. Expressed in equation form, the alarm limit, AL, is:

$$AL = \max(\min(AL_{MAXPA}, AL_{MAXAA}, AL_{MAXDA}, AL_{SDA}) \max(AL_{MINAA}, AL_{MINDA})). \quad (16)$$

The determination of which of the two statistical envelope construction techniques will be applied to construct a statistical envelope first requires a definition of the scope of the analysis. The next step is to determine which machines included in the analysis are considered to be similar such that it is appropriate to combine their data in the envelope construction process. This is done most efficiently by organizing machines with similar vibration signatures into analysis groups.

The next step in choosing which statistical envelope construction technique is to be applied is to determine if individual limit envelopes are to be constructed for individual measurement points that are common to the machines in each analysis group. For example, if data is limited, data can be combined for a given bearing location that is common to a group of machines. This would involve including the spectral data from each spacial orientation (horizontal, vertical, and axial) of the outboard bearing location of the motor component in the construction of single statistical envelope. The limit envelope derived from the statistical spectrum would then be applicable to each of the locations on the machine at which data was measured. If data is very limited, data from all of the measurement points that are present on a given machine can be combined into a single statistical envelope. An example would be taking all of the data previously measured on the motor of a motor/pump apparatus and using this data to create a single statistical spectrum. This statistical spectrum would be used to construct a single alarm limit envelope which would be applied to all of the measurement points associated with the motor.

Figure 7:
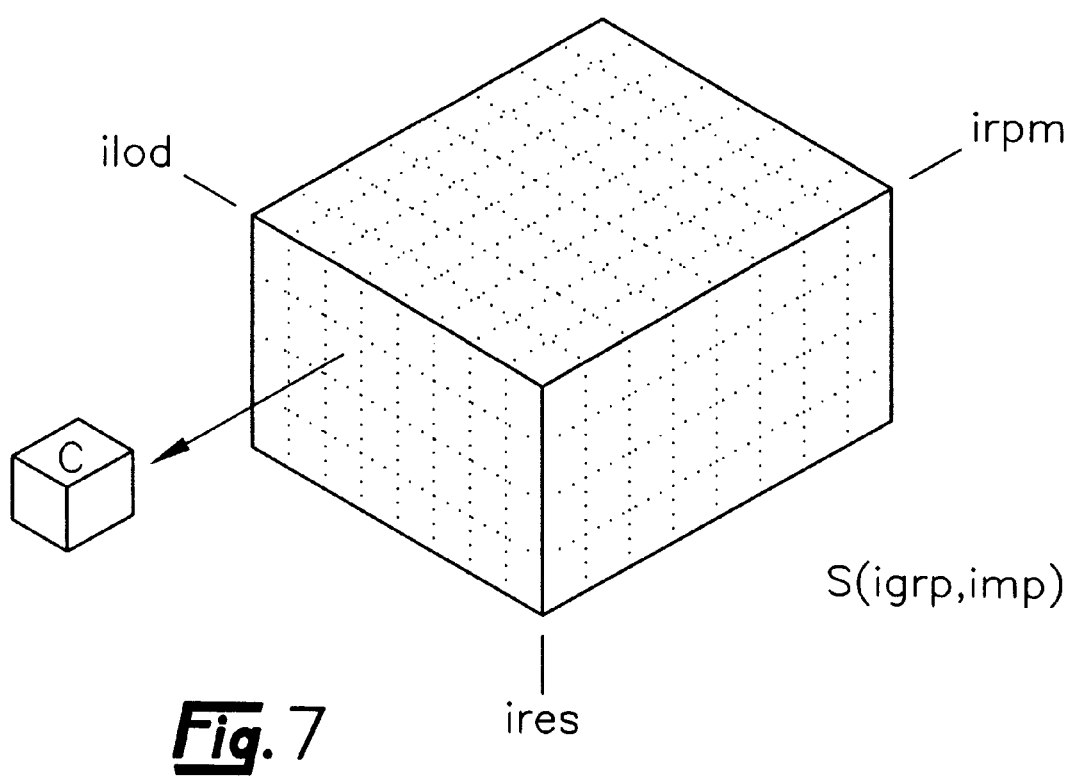
FIG. 7 is a flow diagram of a statistical alarm limit enveloping process according to the present invention.

In a preferred embodiment of the invention, different envelopes can be constructed for the same measurement point/analysis group if the operational parameters of the machine vary significantly. For example, if a group of similar machines is found that commonly runs at 50% load, 75% load, and 100% load, then separate statistical spectra can be constructed so that each set of operational parameters has its own alarm limit envelope. Differences in machine speed and data resolution are also considered in this manner when constructing envelopes. The result is a three-dimensional coverage cube, as shown in FIG. 7, which contains all of the alarm limit envelopes that are applicable for the different operational parameters of a given measurement point and analysis group. The three axes of the cube represent machine speed, data resolution, and machine load. A single set of speed, resolution, and load indices, indicated by C in FIG. 7 represent a certain envelope that was constructed using only data that was taken from a machine when it was operating with those specific parameters. The user may define break-points on the three axis so that the different points on each scale represent what correlates to shifts in operational parameters that could easily result in the machine exhibiting different vibration characteristics. For constant-speed/constant-load machinery where data of the same number of resolution lines have always been measured, this technique would find data for only one set of speed, resolution, and load criteria As a result, only one envelope would be created, and the cube of FIG. 7 would have only one entry of significance.

When spectral data sets are being combined by the processes of the present invention to construct statistical spectra, the validity of each spectrum is tested at three different levels before it is included in the analysis. The first level examines the data from the components associated with the machines that have been grouped together. This validity check attempts to ensure that the machines that have been grouped together are in fact similar. If overall readings of the spectral data from a machine are found to be out of bounds relative to the overall readings of the other machines included in the analysis group, then the data is excluded from the analysis.

The second validity check is performed as each statistical spectrum is constructed. This test examines the overall mean and standard deviation of the data that is being combined from each individual machine relative to the overall mean and standard deviation of the data calculated for all of the machines which contributed to the statistical spectrum. If data for a given spectrum is made up of data from only one machine, then this second validity check has no significance.

The third level of validity checking is performed for each individual spectral data set that is included in the analysis. This check examines the overall reading of each individual spectral data set relative to the mean and standard deviation of the entire group of data that is to be included in the statistical spectrum. If the overall reading from the individual spectrum falls outside a valid range defined by:

$$\text{valid range} = \text{MEAN} \pm (\text{STANDEV} \times \sigma), \tag{17}$$

where MEAN and STANDEV are the mean and the standard deviation of the entire group of spectral data sets, then the individual spectral data set is excluded from the calculation of the statistical spectrum. The variable sigma, $\sigma$, is a function of the number of samples, or number of spectra in this case, that are to be included in the statistical spectrum.

A fourth level of validity check is performed at each line of resolution in the spectra by checking on a line-by-line basis for vibration levels falling outside a valid range. The first step in this test is to combine all of the spectral data sets, on an order-normalized basis, to form a composite statistical spectrum where each line of the composite spectrum has an individually-calculated mean, standard deviation, and number of samples. During this first pass through the data sets, no data is rejected; all of the data is used to determine a vibration level outer limit beyond which "outliers", or vibration levels lying outside the valid range, are rejected. As with the valid range calculation of equation (17), the outlier limit is a function of the number of samples included in the calculation. The outlier limit, calculated on a line-by-line basis is expressed as:

$$\text{outlier limit} = \text{MEAN} + (\text{STANDEV} \times \sigma), \tag{18}$$

where MEAN and STANDEV are the mean and the standard deviation of the vibration levels at each spectral line in the composite spectrum. Each additional pass through the spectral data sets use the outlier limit determined on the previous pass to reject outliers. In a preferred embodiment of the invention, the number of passes to check for outliers is specified by the user. For each additional pass, additional outliers are rejected based on the mean and standard deviation values calculated during the previous pass. Thus, the more construction passes that are requested, the more conservative the final mean and sigma values become.

In a preferred embodiment of the invention, as the number of samples (spectral data sets) included in the composite spectrum falls below fifty, $\sigma$ in equation (18) drops below three. This provides a more conservative limit, since the validity of standard deviation is questionable. As the number of samples included in the composite spectrum becomes greater than fifty, $\sigma$ in equation (18) increases above three. This provides a less conservative limit, since more confidence can be placed in the value of the standard deviation.

It is contemplated, and will be apparent to those skilled in the art from the preceding description and the accompanying drawings that modifications and/or changes may be made in the embodiments of the invention. Accordingly, it is expressly intended that the foregoing description and the accompanying drawings are illustrative of preferred embodiments only, not limiting thereto, and that the true spirit and scope of the present invention be determined by reference to the appended claims.

What is claimed is:

1. A method for constructing an alarm limit envelope for spectral analysis of vibration data collected from a machine, said constructing based on a single measured machine vibration spectrum, the alarm limit envelope representing maximum vibration levels for which measured vibration levels within a measured vibration spectrum are considered normal, the method comprising the steps of:

measuring vibration generated by the machine over time to produce a time series of vibration data measurements;

transforming the time series of vibration data measurements from the time domain to the frequency domain to produce the single measured vibration spectrum consisting of a set of data points, where each data point includes a vibration amplitude level and a corresponding vibration frequency;

dividing said measured vibration spectrum into a plurality of frequency windows which are subsets of the data points having consecutive vibration frequencies, where each window includes a vibration peak which is a data point having the largest vibration amplitude within the window; and calculating an alarm limit value for each window, each of said alarm limit values representing a maximum vibration level above which an amplitude level of any single data point having a vibration frequency within the window is considered abnormal, wherein the alarm limit values for all windows within the measured vibration spectrum collectively comprise an alarm limit envelope.

2. A method for constructing an alarm limit envelope based on a plurality of machine vibration spectra, the alarm limit envelope representing maximum machine vibration levels for which measured vibration levels within a measured machine vibration spectrum are considered normal, the method comprising the steps of:

providing a plurality of vibration spectra corresponding to vibration generated by at least one machine;

determining a mean vibration spectrum based on said plurality of vibration spectra, the mean vibration spectrum consisting of a set of data points, where each data point includes a vibration amplitude level and a corresponding vibration frequency, wherein each amplitude corresponding to a particular frequency in the mean vibration spectrum is a statistical mean of all corresponding amplitude levels of said plurality of vibration spectra;

dividing said mean vibration spectrum into a plurality of frequency windows which are subsets of the data points having consecutive vibration frequencies, where each window includes a mean vibration peak which is a data point having the largest vibration amplitude within the window; and calculating an alarm limit value for each window, each of said alarm limit values representing a maximum vibration level above which an amplitude level of any single data point having a vibration frequency within the window is considered abnormal wherein the alarm limit values for all windows within the mean vibration spectrum collectively comprise an alarm limit envelope.

3. The method of claim 1 wherein said calculating step further comprises:

determining a candidate alarm limit for each window, said candidate alarm limit being based upon the amplitude of the vibration peak in the window; and determining an alarm limit value for each window based on the candidate alarm limit for each window.

4. The method of claim 1 wherein said calculating step further comprises:

determining a plurality of candidate alarm limits for each window;

determining a multiplier that conservatively adjusts at least one of said candidate alarm limits based upon characteristics specific to the vibration peak within the window;

adjusting at least one of said candidate alarm limits in accordance with said multiplier for that candidate alarm limit to produce a plurality of adjusted candidate alarm limits for each window; and selecting one of said adjusted candidate alarm limits to be the alarm limit value for the window.

5. The method of claim 2 wherein said calculating step further comprises:

determining a candidate alarm limit for each window, said candidate alarm limit being based upon the amplitude of the mean vibration peak in the window; and determining an alarm limit value for each window based on the candidate alarm limit for each window.

6. The method of claim 2 wherein said calculating step further comprises:

determining a plurality of candidate alarm limits for each window;

determining a multiplier that conservatively adjusts at least one of said candidate alarm limits based upon characteristics specific to the mean vibration peak within the window;

adjusting at least one of said candidate alarm limits in accordance with said multiplier for that candidate alarm limit to produce a plurality of adjusted candidate alarm limits for each window; and selecting one of said adjusted candidate alarm limits to be the alarm limit value for the window.

7. The method of claim 1 wherein the measured vibration spectrum is an initial vibration spectrum based upon vibration data measurements that are measured on the machine at a time when it is not known whether the machine's vibration is normal.

8. The method of claim 7 wherein each of said alarm limit values further represent a maximum vibration level above which an amplitude level of any single data point in the initial vibration spectrum having a vibration frequency within the window is considered abnormal.

9. The method of claim 1 wherein said calculating step further comprises:

determining a first candidate alarm limit expressed as a percentage of the amplitude of the vibration peak within the window;

determining a second candidate alarm limit expressed as a maximum absolute alarm level that is independent of the amplitude of the vibration peak within the window, where the maximum absolute alarm level is a percentage of a predetermined overall alert level;

determining a third candidate alarm limit expressed as a sum of the amplitude of the vibration peak within the window and a value that is a percentage of the predetermined overall alert level;

determining a fourth candidate alarm limit expressed as a minimum absolute alarm level that is independent of the amplitude of the vibration peak within the window, where the minimum absolute alarm level is a percentage of the predetermined overall alert level;

determining a fifth candidate alarm limit expressed as a difference between the amplitude of the vibration peak within the window and a value that is a percentage of the predetermined overall alert level; and determining an alarm limit value for each window based on the first, second, third, fourth, and fifth candidate alarm limits.

10. The method of claim 9 further comprising adjusting each of said candidate alarm limits to produce first, second, third, fourth, and fifth adjusted candidate alarm limits for each window, and wherein the step of determining an alarm limit value for each window further comprises selecting one of the candidate alarm limits according to:

$$AL = \max(\min(AL_{MAXPA}, AL_{MAXAA}, AL_{MAXDA}), \max(AL_{MINAA}, AL_{MINDA})),$$

17 where:
   AL is the alarm limit value;
   $AL_{MAXPA}$ is the first adjusted candidate alarm limit;
   $AL_{MAXAA}$ is the second adjusted candidate alarm limit;
   $AL_{MAXDA}$ is the third adjusted candidate alarm limit;
   $AL_{MINAA}$ is the fourth adjusted candidate alarm limit; and
   $AL_{MINDA}$ is the fifth adjusted candidate alarm limit.

11. The method of claim 2 wherein said calculating step further comprises:
   determining a first candidate alarm limit expressed as a percentage of the amplitude of the mean vibration peak within the window;
   determining a second candidate alarm limit expressed as a maximum absolute alarm level that is independent of the amplitude of the mean vibration peak within the window, where the maximum absolute alarm level is a percentage of a predetermined overall alert level;
   determining a third candidate alarm limit expressed as a sum of the amplitude of the mean vibration peak within the window and a value that is a percentage of the predetermined overall alert level;
   determining a fourth candidate alarm limit expressed as a minimum absolute alarm level that is independent of the amplitude of the mean vibration peak within the window, where the minimum absolute alarm level is a percentage of the predetermined overall alert level;
   determining a fifth candidate alarm limit expressed as a difference between the amplitude of the mean vibration peak within the window and a value that is a percentage of the predetermined overall alert level; and
   determining an alarm limit value for each window based on the first, second, third, fourth, and fifth candidate alarm limits.

12. The method of claim 11 further comprising adjusting each of said candidate alarm limits to produce first, second, third, fourth, and fifth adjusted candidate alarm limits for each window, and wherein the step of determining an alarm limit value for each window further comprises selecting one of the candidate alarm limits according to:

$$AL=\max(\min(AL_{MAXPA}, AL_{MAXAA}, AL_{MAXDA}) \max(AL_{MINAA}, AL_{MINDA})),$$

where:
   AL is the alarm limit value;
   $AL_{MAXPA}$ is the first adjusted candidate alarm limit;
   $AL_{MAXAA}$ is the second adjusted candidate alarm limit;
   $AL_{MAXDA}$ is the third adjusted candidate alarm limit;
   $AL_{MINAA}$ is the fourth adjusted candidate alarm limit; and
   $AL_{MINDA}$ is the fifth adjusted candidate alarm limit.

13. The method of claim 2 further comprising:
   determining a standard deviation vibration spectrum based on said plurality of vibration spectra, the standard deviation vibration spectrum consisting of a set of data points, where each data point includes a standard deviation vibration amplitude level and a corresponding vibration frequency, wherein each amplitude level corresponding to a particular frequency in the standard deviation vibration spectrum is a statistical standard deviation of all corresponding amplitude levels of said plurality of vibration spectra; and
   determining a candidate alarm limit based on mean vibration amplitude levels and standard deviation vibration amplitude levels.

18

14. The method of claim 13 wherein said calculating step further comprises:
   determining a first candidate alarm limit expressed as a percentage of the amplitude of the mean vibration peak within the window;
   determining a second candidate alarm limit expressed as a maximum absolute alarm level that is independent of the amplitude of the mean vibration peak within the window, where the maximum absolute alarm level is a percentage of a predetermined overall alert level;
   determining a third candidate alarm limit expressed as a sum of the amplitude of the mean vibration peak within the window and a value that is a percentage of the predetermined overall alert level;
   determining a fourth candidate alarm limit expressed as a minimum absolute alarm level that is independent of the amplitude of the mean vibration peak within the window, where the minimum absolute alarm level is a percentage of the predetermined overall alert level;
   determining a fifth candidate alarm limit expressed as a difference between the amplitude of the mean vibration peak within the window and a value that is a percentage of the predetermined overall alert level;
   determining a sixth candidate alarm limit according to:

$$AL_{SDA}=\max\{MEAN_i+(SDA \times STANDEV_i)\}$$

for i=1 to n, where n is the number of data points in the window, and where:
   $AL_{SDA}$ is the sixth candidate alarm limit,
   $MEAN_i$ is a mean vibration amplitude level at the ith data point in the data window,
   $STANDEV_i$ is a standard deviation vibration amplitude level at the ith data point in the data window, and
   SDA is a user-selectable value; and
   determining an alarm limit value for each window based on the first, second, third, fourth, fifth, and sixth candidate alarm limits.

15. The method of claim 14 further comprising adjusting each of said candidate alarm limits to produce first, second, third, fourth, and fifth adjusted candidate alarm limits for each window, and wherein the step of determining an alarm limit value for each window further comprises selecting one of the candidate alarm limits according to:

$$AL=\max(\min(AL_{MAXPA}, AL_{MAXAA}, AL_{MAXDA}, AL_{SDA}) \max(AL_{MINAA}, AL_{MINDA})),$$

where:
   AL is the alarm limit value;
   $AL_{MAXPA}$ is the first adjusted candidate alarm limit;
   $AL_{MAXAA}$ is the second adjusted candidate alarm limit;
   $AL_{MAXDA}$ is the third adjusted candidate alarm limit;
   $AL_{MINAA}$ is the fourth adjusted candidate alarm limit;
   $AL_{MINDA}$ is the fifth adjusted candidate alarm limit; and
   $AL_{SDA}$ is the sixth candidate alarm limit.

16. A machine vibration monitoring system for measuring and analyzing mechanical vibration levels of a machine to determine an operational condition of the machine, where the vibration levels are represented by a frequency-domain vibration spectrum, the system comprising:
   a computer for analyzing the frequency-domain vibration spectrum, for determining an alarm limit envelope based on the frequency-domain vibration spectrum where the alarm limit envelope represents a maximum vibration level above which the vibration levels of the machine are considered abnormal, and for determining whether the machine's vibration levels exceed the alarm limit envelope, the computer comprising:

a computer processor for
- dividing the vibration spectrum into a plurality of frequency windows that are subsets of data points having consecutive vibration frequencies, where each window includes a vibration peak which is a data point having the largest vibration amplitude within the window,
- calculating an alarm limit value for each window, the alarm limit value representing a maximum vibration level above which an amplitude level of any single data point having a vibration frequency within the window is considered abnormal, and
- assembling the alarm limit values for all windows within the vibration spectrum to construct the alarm limit envelope;

computer memory connected to the computer processor for storing the vibration spectrum and the alarm limit envelope;

a user interface connected to the computer processor for providing operator control system functions; and a display connected to the computer processor for providing visual representations used in controlling system functions, and for viewing the vibration spectrum and the alarm limit envelope.

17. The machine vibration monitoring system of claim 16 wherein the computer processor further determines a candidate alarm limit for each window based upon the amplitude of the vibration peak in the window, and determines the alarm limit value for each window based on the candidate alarm limit for each window.

18. The machine vibration monitoring system of claim 16 wherein the computer processor further determines a plurality of candidate alarm limits for each window, determines a multiplier that conservatively adjusts at least one of said candidate alarm limits based upon characteristics specific to the vibration peak within the window, adjusts at least one of said candidate alarm limits in accordance with said multiplier for that candidate alarm limit to produce a plurality of adjusted candidate alarm limits for each window, and selects one of said adjusted candidate alarm limits to be the alarm limit value for the window.

19. The machine vibration monitoring system of claim 16 further comprising a portable vibration analyzer for collecting and storing vibration information that indicates the vibration levels of the machine, the portable vibration analyzer comprising:

a sensor for converting the mechanical vibration levels of the machine into a time-domain electrical signal representing the mechanical vibration levels of the machine;

a signal conditioning circuit for filtering, amplifying, and converting the time-domain electrical signal into a format that can be digitally processed;

a signal transformation circuit for transforming the time-domain electrical signal into a frequency-domain vibration spectrum representing the mechanical vibration levels of the machine, the vibration spectrum consisting of a set of data points, where each data point includes a vibration amplitude level and a corresponding vibration frequency; and analyzer memory for storing the frequency-domain vibration spectrum.

* * * * *

UNITED STATES PATENT AND TRADEMARK OFFICE
CERTIFICATE OF CORRECTION

PATENT NO : 5,922,963
DATED : July 13, 1999
INVENTOR(S): Piety et al.

It is certified that error appears in the above-identified patent and that said Letters Patent is hereby corrected as shown below:

At Column 7, line 28, after "Using" and before ", the alarm", delete "A" and insert therefor --MAXPA--.

At Column 7, line 55, delete equation (2) and insert therefor:

$$AL_{MAXAA} = \frac{MAXAA \times FMLT}{100} \times OAL \tag{2}$$

At Column 8, line 34, delete equation (5) and insert therefor:

$$AL_{MINDA} = PVL - \left(\frac{MINDA \times CMLT}{100} \times OAL\right) \tag{5}$$

At Column 8, line 51, delete the equation (6) and insert therefor:

$$AL = \max\left(\min\left(AL_{MAXPA}, AL_{MAXAA}, AL_{MAXDA}\right), \max\left(AL_{MINAA}, AL_{MINDA}\right)\right) \tag{6}$$

At Column 9, line 37, after "TOL" and before "0.060", insert -- = --.

At Column 15, line 28, before "corresponding" add --level--.

UNITED STATES PATENT AND TRADEMARK OFFICE
CERTIFICATE OF CORRECTION

PATENT NO : 5,922,963
DATED : July 13, 1999
INVENTOR(S) : Piety et al.

It is certified that error appears in the above-identified patent and that said Letters Patent is hereby corrected as shown below:

At Column 16, line 67, delete the equation and insert therefor:

$$AL = \max\left(\min\left(AL_{MAXPA}, AL_{MAXAA}, AL_{MAXDA}\right), \max\left(AL_{MINAA}, AL_{MINDA}\right)\right)$$

At Column 18, line 28, delete the equation and insert therefor:

$$AL_{SDA} = \max\left[MEAN_i + (SDA \times STANDEV_i)\right]$$

Signed and Sealed this

Eighteenth Day of April, 2000

Q. TODD DICKINSON

*Attest:*

*Attesting Officer*  *Director of Patents and Trademarks*